(12) United States Patent
Erb et al.

(10) Patent No.: US 9,776,966 B2
(45) Date of Patent: Oct. 3, 2017

(54) SYNTHESIS OF 2-CARBOXAMIDE CYCLOAMINO UREA DERIVATIVES

(71) Applicant: Novartis AG, Basel (CH)

(72) Inventors: Bernhard Erb, Gipf-Oberfrick (CH); Isabelle Sylvie Gallou, Binningen (CH); Florian Karl Kleinbeck, Zurich (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/480,835

(22) Filed: Apr. 6, 2017

(65) Prior Publication Data

US 2017/0240509 A1    Aug. 24, 2017

Related U.S. Application Data

(62) Division of application No. 13/985,069, filed as application No. PCT/EP2012/053559 on Mar. 1, 2012, now Pat. No. 9,650,373.

(60) Provisional application No. 61/448,774, filed on Mar. 3, 2011.

(51) Int. Cl.
| | |
|---|---|
| *C07D 417/04* | (2006.01) |
| *C07D 417/14* | (2006.01) |
| *C07D 211/72* | (2006.01) |
| *C07D 211/84* | (2006.01) |
| *C07D 213/26* | (2006.01) |

(52) U.S. Cl.
CPC ................... *C07D 213/26* (2013.01)

(58) Field of Classification Search
None
See application file for complete search history.

(56) References Cited

FOREIGN PATENT DOCUMENTS

| WO | 99/62890 A1 | 12/1999 |
|---|---|---|
| WO | 01/17995 A1 | 3/2001 |
| WO | 2004/096797 A1 | 11/2004 |
| WO | 2007/087427 A2 | 8/2007 |
| WO | 2009/080694 A1 | 7/2009 |
| WO | 2010/029082 A1 | 3/2010 |

OTHER PUBLICATIONS

Gallagher, Sai. et al. Aromatic N-Oxides. V. The Reaction of 4-Picoline N-Oxide with Various Anhydrides. JACS. 1965, vol. 87, p. 5714.*
Sarkis G Y et al: "Preparation and spectral characterization of substituted 2-aminothiazoles", Journal of Chemical and Engineering Data, American Chemical Society, US, vol. 18, No. 1, Jan. 1, 1973, pp. 99-102.
Gallagher, Sai. et al,, "Aromatic N-Oxides. V. The Reaction of 4-Picoline N-Oxide with Various Anhydrides", Journal of the American Chemical Society. 1965, vol. 87, p. 5714.

* cited by examiner

*Primary Examiner* — Noble Jarrell
*Assistant Examiner* — Ben S Michelson
(74) *Attorney, Agent, or Firm* — Michelle A. Han

(57) ABSTRACT

Provided herein are processes and intermediate compounds useful for the preparation of 2-carboxamide cycloamino urea derivatives, and useful intermediates therefore.

1 Claim, No Drawings

SYNTHESIS OF 2-CARBOXAMIDE CYCLOAMINO UREA DERIVATIVES

FIELD OF INVENTION

The present invention is directed to processes for preparing 2-carboxamide cycloamino urea derivatives, and useful intermediates therefore.

BACKGROUND

The processes of the present invention are useful for the preparation of alpha-selective phosphatidylinositol (PI) 3-kinase inhibitor compounds according to formula (X), and intermediates therefore. Phosphatidylinositol 3-kinases (PI3Ks) comprise a family of lipid kinases that catalyze the transfer of phosphate to the D-3' position of inositol lipids to produce phosphoinositol-3-phosphate (PIP), phosphoinositol-3,4-diphosphate (PIP2) and phosphoinositol-3,4,5-triphosphate (PIP3), which, in turn, act as second messengers in signaling cascades by docking proteins containing pleckstrin-homology, FYVE, Phox and other phospholipid-binding domains into a variety of signaling complexes often at the plasma membrane.

PCT Publication No. WO 20101029082 discloses PI3K inhibitors. The compounds disclosed therein include (S)-pyrrolidine-1,2-dicarboxylic acid 2-amide 1-({4-methyl-5-[2-(2,2,2-trifluoro-1,1-dimethyl-ethyl)-pyridin-4-yl]-thiazol-2-yl}-amide) (i.e., the compound of formula (10)). The present invention is directed to improved processes for preparing compounds of the formula (X), specifically the compound of formula (10), as well as useful intermediates such as compounds of the formula (I), specifically the compound of formula (1):

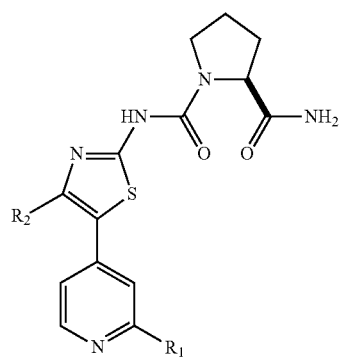
(X)

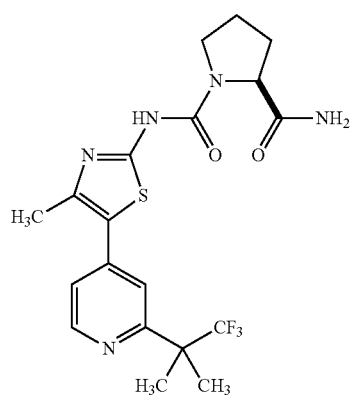
(10)

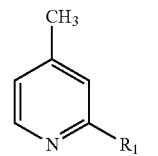
(I)

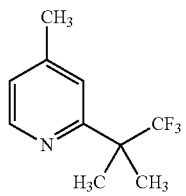
(1)

SUMMARY OF THE INVENTION

Provided herein are processes for the preparation of compounds of formula (X). Also provided herein are intermediate compounds, as well as methods of making those intermediates, that are useful for the preparation of compounds of formula (X). The compounds of formulas (I)-(X) and the compounds of formulas (1) to (8) and (10) refer to the compounds as defined in the description herein.

In one aspect, provided herein is a process for making a compound of formula (V)

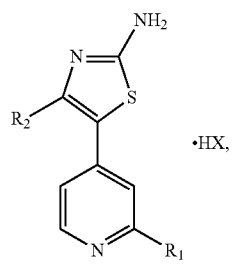
(V)

comprising contacting a compound of formula (I) with a solvent and a base and contacting the resulting mixture with a compound of formula (II), such that a compound of formula (III) is produced (STEP A). The compound of formula (III) is then contacted with thiourea, in a reaction mixture comprising a solvent and an oxidizing agent, such that a compound of formula (V) is produced (STEP B).

In another aspect, provided herein is a process for making a compound of formula (X)

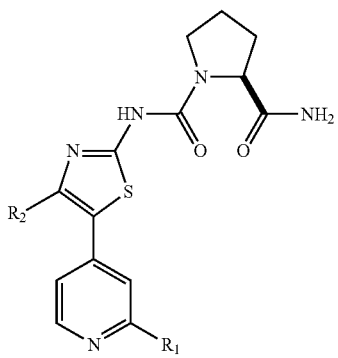
(X)

comprising contacting a compound of formula (V) with a compound of formula (VII), in a reaction mixture comprising a solvent and a base, such that a compound of formula (VIII) is produced (STEP C). The compound of formula (VIII) is then contacted with the compound of formula (IX) in a reaction mixture comprising a solvent, such that a compound of formula (X) is produced (STEP D).

In still another aspect, provided herein is a process for making a compound of formula (X), comprising contacting a compound of formula (I) with a solvent and a base, and contacting the resulting mixture with a compound of formula (II), such that a compound of formula (III) is produced (STEP A); contacting a compound of formula (III) with thiourea, in a reaction mixture comprising a solvent and an oxidizing agent, such that a compound of formula (V) is produced (STEP B); contacting a compound of formula (V) with a compound of formula (VII), in a reaction mixture comprising a solvent and a base, such that a compound of formula (VIII) is produced (STEP C); and contacting a compound of formula (VIII) with the compound of formula (IX) in a reaction mixture comprising a solvent, such that a compound of formula (X) is produced (STEP D).

In accordance with the present invention, the solvent of Step A comprises one or more solvents selected from aromatic solvents, aliphatic solvents, halogenated solvents, polar aprotic solvents and ethereal solvents.

In accordance with the present invention, the solvent of Steps B, C and D independently comprises one or more solvents selected from aromatic solvents, aliphatic solvents, halogenated solvents, ethereal solvents, polar aprotic solvents, water and alcohol solvents.

In yet another aspect, provided herein is a process for making the compound of formula (10), comprising contacting the compound of formula (1) with a solvent and a base, and contacting the resulting mixture with a compound of formula (2), such that the compound of formula (3) is produced (STEP A). The compound of formula (3) is then contacted with thiourea, in a reaction mixture comprising a solvent and an oxidizing agent, such that the compound of formula (5) is produced (STEP B). The compound of formula (5) is next contacted with the compound of formula (7), in a reaction mixture comprising a solvent and a base, such that the compound of formula (8) is produced (STEP C). Finally, the compound of formula (8) is contacted with the compound of formula (IX), in a reaction mixture comprising a solvent, such that the compound of formula (10) is produced (STEP D).

In one embodiment of the synthesis of the compound of formula (10), the solvent of Step A comprises tetrahydrofuran, the base of Step A is lithium diisopropylamide, the solvent of Step B comprises toluene and ethanol, the oxidizing agent of Step B is N-bromosuccinimide, the solvent of Step C comprises tetrahydrofuran, the base of Step C is pyridine and the solvent of Step D comprises tetrahydrofuran and water.

In another aspect, provided herein is a compound according to formula (1).

DETAILED DESCRIPTION

Provided herein are processes and intermediate compounds useful for the preparation of PI3K inhibitors. These processes are advantageous over previously-known processes (see, e.g., PCT Publication No. WO 2010/029082) in several ways. For example, the instant processes do not employ transition metal-catalyzed reactions, and therefore do not require steps to remove transition metal byproducts, residues and impurities. Additionally, the instant processes do not require reactions to be performed at very low temperatures (e.g., −78° C.).

In one aspect of the present invention, provided herein is a process for making a compound of formula (V), comprising the following steps:

Step A: contacting a compound of formula (I) with a solvent and a base, and contacting the resulting mixture with a compound of formula (II), such that a compound of formula (III) is produced:

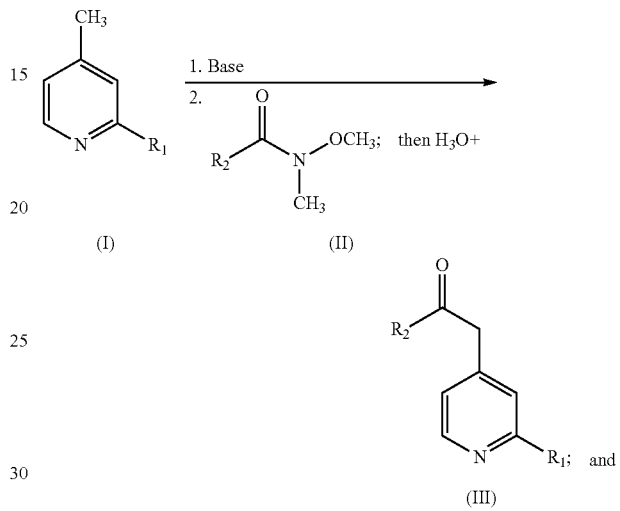

Step B: contacting a compound of formula (III) with thiourea, in a reaction mixture comprising a solvent and an oxidizing agent [X+], such that a compound of formula (V) is produced:

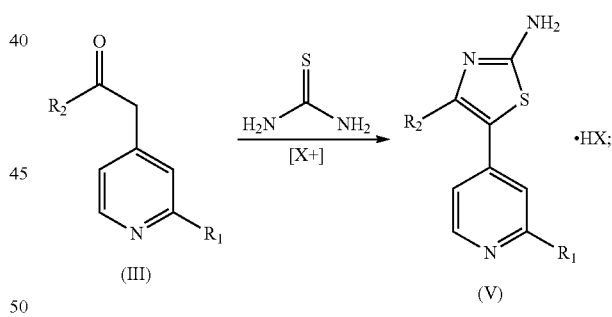

wherein $R_1$ is a cyclic or acyclic, branched or linear $C_1$-$C_3$ alkyl, which may be optionally substituted one or more times with deuterium, halogen, or $C_3$-$C_5$ cycloalkyl; and wherein $R_2$ is selected from (1) hydrogen, (2) fluoro, chloro, (3) optionally substituted methyl, wherein said substituents are independently selected from one or more, preferably one to three of the following moieties: deuterium, fluoro, choro, dimethylamino; and wherein X is selected from the group consisting of halide, carboxylate and sulfonate.

In another aspect, provided herein is a process for making a compound of formula (X), comprising the following steps:

Step C: contacting a compound of formula (V) with a compound of formula (VII), in a reaction mixture comprising a solvent and a base, such that a compound of formula (VIII) is produced:

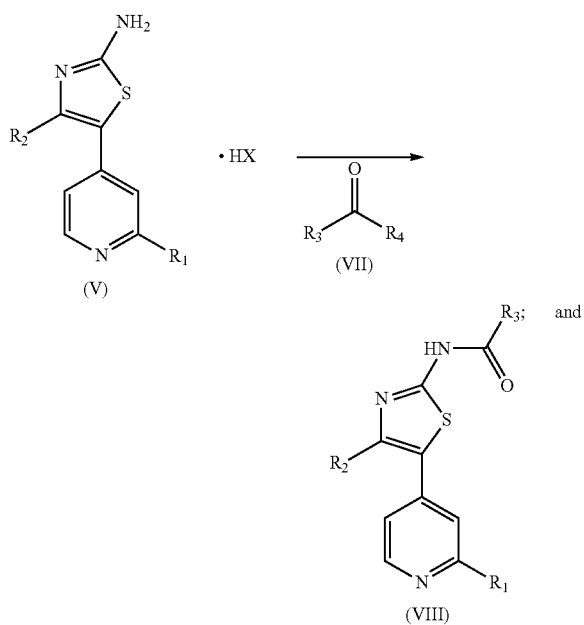

Step D: contacting a compound of formula (VIII) with the compound of formula (IX), in a reaction mixture comprising a solvent, such that a compound of formula (X) is produced:

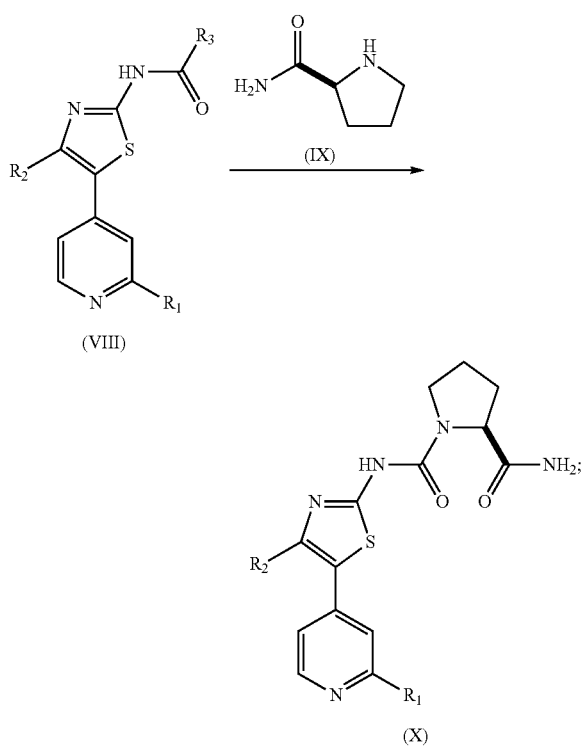

wherein $R_1$ is a cyclic or acyclic, branched or linear $C_1$-$C_7$ alkyl, which may be optionally substituted one or more times with deuterium, halogen, or $C_3$-$C_5$ cycloalkyl; and wherein $R_2$ is selected from (1) hydrogen, (2) fluoro, chloro, (3) optionally substituted methyl, wherein said substituents are independently selected from one or more, preferably one to three of the following moieties: deuterium, fluoro, chloro, dimethylamino; and wherein X is selected from the group consisting of halide, carboxylate and sulfonate; and wherein $R_3$ and $R_4$ are independently selected from the group consisting of halogen, heteroaryl, alkoxy and aryloxy; and wherein the heteroaryl, alkoxy and aryloxy moieties of $R_3$ and $R_4$ are optionally, independently substituted one or more times with alkyl, alkoxy, halogen and nitro.

In still another aspect, provided herein is a process for making a compound of formula (X), comprising the following steps: Step A: contacting a compound of formula (I) with a solvent and a base, and contacting the resulting mixture with a compound of formula (II), such that a compound of formula (III) is produced; Step B: contacting a compound of formula (III) with thiourea, in a reaction mixture comprising a solvent and an oxidizing agent, such that a compound of formula (V) is produced; Step C: contacting a compound of formula (V) with a compound of formula (VII), in a reaction mixture comprising a solvent and a base, such that a compound of formula (VIII) is produced; and Step D: contacting a compound of formula (VIII) with the compound of formula (IX), in a reaction mixture comprising a solvent, such that a compound of formula (X) is produced; wherein $R_1$, $R_2$, $R_3$, $R_4$ and X are as defined above.

In accordance with the present invention, the solvent of Step A comprises one or more solvents selected from aromatic solvents, aliphatic solvents, halogenated solvents, polar aprotic solvents and ethereal solvents. Numerous examples of these solvents are known to those with skill in the art. Non-limiting examples of aromatic solvents include benzene, toluene, xylenes, nitrobenzene, anisole, ethylbenzene, and pyridine. Non-limiting examples of aliphatic solvents include petroleum ether, ligroin, n-hexane, cyclohexane and heptane. Non-limiting examples of halogenated solvents include chloroform, chlorobenzene and perfluorohexane. Non-limiting examples of polar aprotic solvents include dimethylsulfoxide, dimethylformamide and N-methyl pyrrolidone. Non-limiting examples of ethereal solvents include diethyl ether, methyl tertiary-butyl ether, tetrahydrofuran, 2-methyl tetrahydrofuran and dimethoxyethane. In certain embodiments, the solvent of Step A is an aprotic, organic solvent. In preferred embodiments, the solvent of Step A comprises tetrahydrofuran.

In accordance with the present invention, the solvent of Steps B, C and D independently comprises one or more solvents selected from aromatic solvents, aliphatic solvents, halogenated solvents, ethereal solvents, polar aprotic solvents, water and alcohol solvents. Non-limiting examples of alcohol solvents include ethanol, tertiary-butanol and ethylene glycol. Other alcohol solvents are known to those skilled in the art. In certain embodiments, the solvent of Step B comprises an aromatic solvent and an alcohol solvent. In a preferred embodiment, the solvent of Step B comprises toluene and ethanol. In certain embodiments, the solvent of Step C comprises an ethereal solvent. In a preferred embodiment, the solvent of Step C comprises tetrahydrofuran. In certain embodiments, the solvent of Step D comprises and ethereal solvent and water. In a preferred embodiment, the solvent of Step D comprises tetrahydrofuran and water.

In accordance with the present invention, the base of Step A is a strong base. Strong bases include the conjugate bases of hydrocarbons, ammonia, amines and dihydrogen. Non-limiting examples of strong bases include n-butyllithium, n-hexyllithium, sodium hydride and lithium diisopropylamide. Other strong bases are known to those skilled in the art.

In certain embodiments, the base of Step A is lithium diisopropylamide. Methods of preparing lithium diisopropylamide are known to those of skill in the art (see, e.g., Smith, A. P.; Lamba, J. J. S.; Fraser, C. L., Org. Syn. Col. Vol. 10: 107, (2004)). In one embodiment, the lithium diisopropylamide is prepared by the deprotonation of isopropylamine with an alkyllithium base such as n-butyllithium, n-hexyllithium or n-octyllithium. Safety and economic considerations may influence the selection of reagents used for the preparation of lithium diisopropylamide (see, e.g., Chapter 3: Reagent Selection, in "Practical Process Research and Development", Academic Press, 2000). In one embodiment, the lithium diisopropylamide is prepared by the deprotonation of diisopropylamine with n-hexyllithium. One of skill in the art would understand that solutions of lithium diisopropylamide in certain solvents, such as THF, should be maintained at temperatures equal to or below 0° C.

In one embodiment of the above processes, the base of Step C is an amine. Non-limiting examples of amine bases include tertiary-butylamine, piperidine, triethylamine, 1,8-Diazabicyclo[5.4.0]undec-7-ene and pyridine. Other amine bases are known to those skilled in the art. In certain embodiments, the base of Step C is pyridine.

In accordance with the present invention, the oxidizing agent of Step B is an electrophilic halogen reagent. Numerous electrophilic halogen reagents are known to the skilled practitioner, including dibromine, diiodine, dichlorine, sulfuryl chloride, N-bromosuccinimide, N-iodosuccinimide, N-chlorosuccinimide and 1,3-dibromo-5,5-dimethylhydantoin. In certain embodiments, the oxidizing agent of Step B is N-bromosuccinimide.

In one embodiment of the present invention, the oxidizing agent of Step B is N-bromosuccinimide, and the subsequent mixture is diluted with an anti-solvent agent. In a preferred embodiment, the anti-solvent is isopropyl acetate.

In accordance with the present invention, X is selected from the group consisting of halide, carboxylate, and sulfonate. In certain embodiments, X is a halide. In a preferred embodiment, X is bromine.

In a preferred embodiment of the above processes, the solvent of Step A comprises tetrahydrofuran, the base of Step A is lithium diisopropylamide, the solvent of Step B comprises toluene and ethanol, the oxidizing agent of Step B is N-bromosuccinimide, the solvent of Step C comprises tetrahydrofuran, the base of Step C is pyridine and the solvent of Step D comprises tetrahydrofuran and water.

In various embodiments of the above processes, $R_1$ is a cyclic or acyclic, branched or linear $C_1$-$C_7$ alkyl, all of which may be optionally substituted one or more times with deuterium, halogen, or $C_3$-$C_5$ cycloalkyl. In other embodiments, $R_1$ is a branched or linear $C_1$-$C_7$ alkyl that is optionally substituted one or more times with halogen. In a preferred embodiment, $R_1$ is

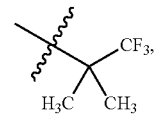

In various embodiments of the above processes, $R_2$ represents (1) hydrogen, (2) fluoro, chloro, (3) optionally substituted methyl, wherein said substituents are independently selected from one or more, preferably one to three of the following moieties: deuterium, fluoro, chloro, dimethylamino. In certain embodiments, $R_2$ is selected from hydrogen, cyclic or acyclic, branched or linear $C_1$-$C_7$ alkyl, and halogen wherein the alkyl is optionally substituted one or more times with deuterium, fluorine, chlorine and dimethylamino. In other embodiments, $R_2$ is a branched or linear $C_1$-$C_7$ alkyl. In a preferred embodiment, $R_2$ is methyl.

In various embodiments, $R_3$ and $R_4$ are independently selected from the group consisting of halogen, heteroaryl, alkoxy and aryloxy; wherein the heteroaryl, alkoxy and aryloxy moieties of $R_3$ and $R_4$ are optionally, independently substituted one or more times with alkyl, alkoxy, halogen and nitro. In certain embodiments, $R_3$ is aryloxy and $R_4$ are both heteroaryl. In other embodiments, $R_3$ is aryloxy and $R_4$ is halogen. In a preferred embodiment, $R_3$ is phenoxy and $R_4$ is chlorine.

In a preferred embodiment of the above processes, $R_1$ is

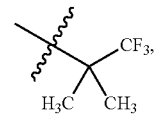

$R_2$ is methyl, $R_3$ is phenoxy, $R_4$ is chlorine and X is bromine.

In one embodiment of the present invention, the compound of formula (I) is first contacted with the compound of formula (II) in a reaction mixture comprising a base and solvent, and second optionally contacted with a reaction mixture comprising an aqueous acid or base resulting in the pH of the aqueous phase to be within the range 2<pH<4, preferably pH 3. Preferably, the base is lithium diisopropylamide and the first solvent is THF, wherein the reaction mixture is maintained such that the internal temperature remains less than −5° C., preferably at −15° C. Preferably, the pH of the aqueous phase is adjusted to pH 3 with a reaction mixture comprising sulfuric acid, water and toluene.

In one embodiment of the present invention, the compound of formula (VIII) is contacted with the compound of formula (IX) in a reaction mixture comprising a first solvent, such that the compound of formula (X) is formed. An aromatic solvent is then added to the mixture, followed by removal of the first solvent by distillation, resulting in the precipitation of the compound of formula (X). Preferably, the aromatic solvent is toluene.

In another aspect of the present invention, provided herein is a process for making the compound of formula (10), comprising the following steps:

Step A: contacting the compound of formula (1) with a solvent and a base, and contacting the resulting mixture with the compound of formula (2), such that the compound of formula (3) is produced:

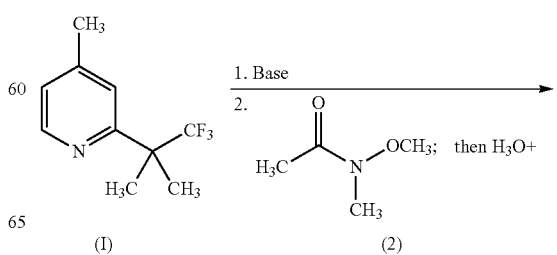

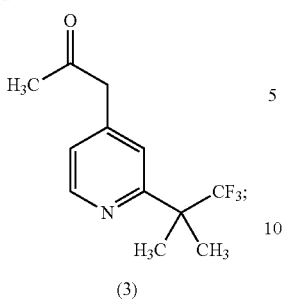

Step B: contacting the compound of formula (3) with thiourea, in a reaction mixture comprising a solvent and an oxidizing agent [Br+], such that the compound of formula (5) is produced:

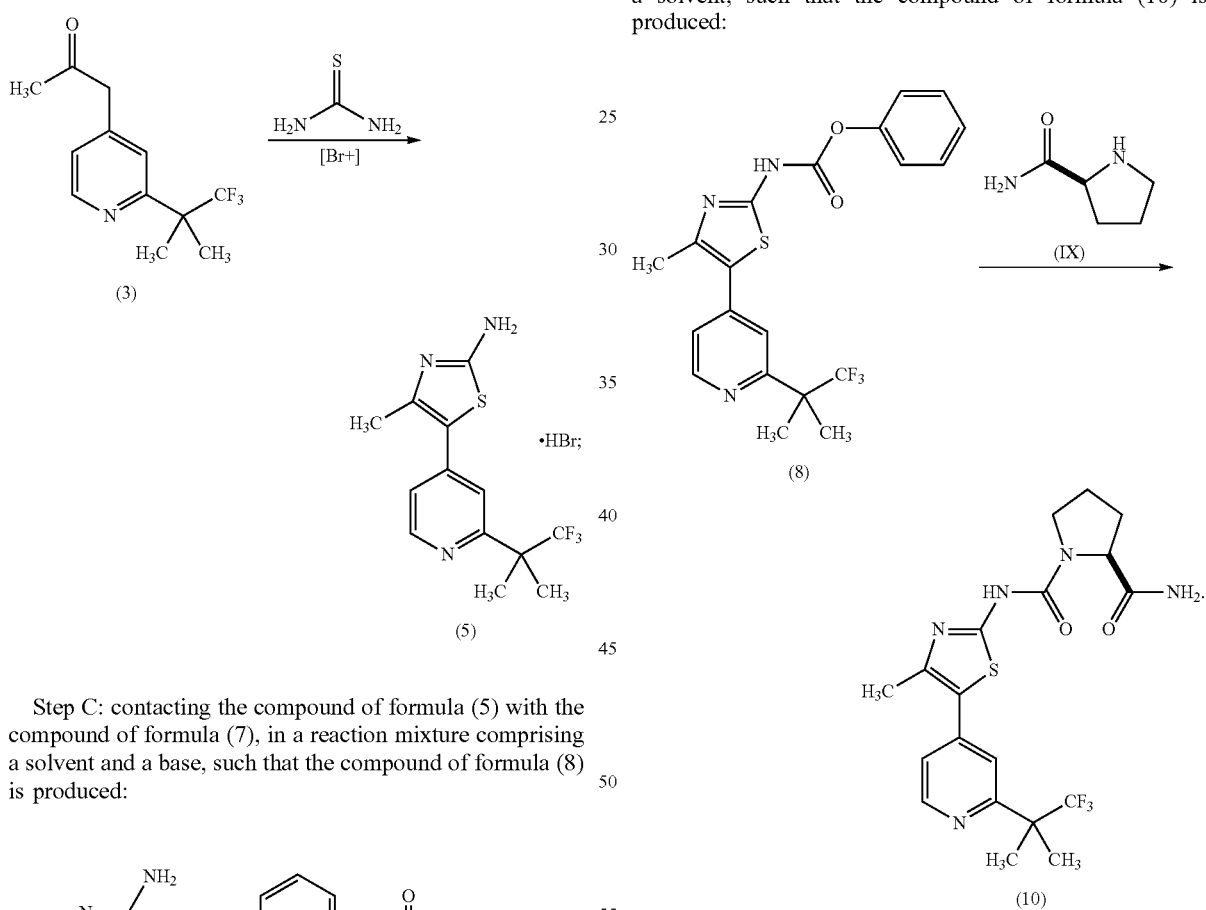

Step C: contacting the compound of formula (5) with the compound of formula (7), in a reaction mixture comprising a solvent and a base, such that the compound of formula (8) is produced:

Step D: contacting the compound of formula (8) with the compound of formula (IX), in a reaction mixture comprising a solvent, such that the compound of formula (10) is produced:

In accordance with this aspect of the present invention, the solvent of Step A comprises one or more solvents selected from aromatic solvents, aliphatic solvents, halogenated solvents, polar aprotic solvents and ethereal solvents. Numerous examples of these solvents are known to those with skill in the art. Non-limiting examples of aromatic solvents include benzene, toluene, xylenes, nitrobenzene, anisole, ethylbenzene, and pyridine. Non-limiting examples of aliphatic solvents include petroleum ether, ligroin, n-hexane, cyclohexane and heptane. Non-limiting examples of halogenated solvents include chloroform, chlorobenzene and perfluorohexane. Non-limiting examples of polar aprotic solvents include dimethylsulfoxide, dimethylformamide and N-methyl pyrrolidone. Non-limiting examples of ethereal solvents include diethyl ether, methyl tertiary-butyl ether, tetrahydrofuran, 2-methyl tetrahydrofuran and dimethoxyethane. In certain embodiments, the solvent of Step A is an aprotic, organic solvent. In preferred embodiments, the solvent of Step A comprises tetrahydrofuran.

In accordance with this aspect of the present invention, the solvent of Steps B, C and D independently comprises one or more solvents selected from aromatic solvents, aliphatic solvents, halogenated solvents, ethereal solvents, polar aprotic solvents, water and alcohol solvents. Non-limiting examples of alcohol solvents include ethanol, tertiary-butanol and ethylene glycol. Other alcohol solvents are known to those skilled in the art. In certain embodiments, the solvent of Step B comprises an aromatic solvent and an alcohol solvent. In a preferred embodiment, the solvent of Step B comprises toluene and ethanol. In certain embodiments, the solvent of Step C comprises an ethereal solvent. In a preferred embodiment, the solvent of Step C comprises tetrahydrofuran. In certain embodiments, the solvent of Step D comprises and ethereal solvent and water. In a preferred embodiment, the solvent of Step D comprises tetrahydrofuran and water.

In accordance with this aspect of the present invention, the base of Step A is a strong base. Strong bases include the conjugate bases of hydrocarbons, ammonia, amines and dihydrogen. Non-limiting examples of strong bases include n-butyllithium, n-hexyllithium, sodium hydride and lithium diisopropylamide. Other strong bases are known to those skilled in the art. In certain embodiments, the base of Step A is lithium diisopropylamide. Methods of preparing lithium diisopropylamide are known to those of skill in the art (see, e.g., Smith, A. P.; Lamba, J. J. S.; Fraser, C. L., Org. Syn. Col. Vol. 10: 107, (2004)). In one embodiment, the lithium diisopropylamide is prepared by the deprotonation of isopropylamine with an alkyllithium base such as n-butyllithium, n-hexyllithium or n-octyllithium. Safety and economic considerations may influence the selection of reagents used for the preparation of lithium diisopropylamide (see, e.g., Chapter 3: Reagent Selection, in "Practical Process Research and Development", Academic Press, 2000). In one embodiment, the lithium diisopropylamide is prepared by the deprotonation of diisopropylamine with n-hexyllithium. One of skill in the art would understand that solutions of lithium diisopropylamide in certain solvents, such as THF, should be maintained at temperatures equal to or below 0° C.

In a further embodiment of the above processes of the present invention, the base of Step C is an amine. Non-limiting examples of amine bases include tertiary-butylamine, piperidine, triethylamine, 1,8-Diazabicyclo[5.4.0]undec-7-ene and pyridine. Other amine bases are known to those skilled in the art. In certain embodiments, the base of Step C is pyridine.

In one embodiment of the above processes of the present invention, the oxidizing agent of Step B is an electrophilic halogen reagent. Numerous electrophilic halogen reagents are known to the skilled practitioner, including dibromine, diiodine, dichlorine, sulfuryl chloride, N-bromosuccinimide, N-iodosuccinimide, N-chlorosuccinimide and 1,3-dibromo-5,5-dimethylhydantoin. In certain embodiments, the oxidizing agent of Step B is N-bromosuccinimide.

In one embodiment of the present invention, the oxidizing agent of Step B is N-bromosuccinimide, and the subsequent mixture is diluted with an anti-solvent agent. In a preferred embodiment, the anti-solvent is isopropyl acetate.

In a preferred embodiment of the synthesis of the compound of formula (10), the solvent of Step A comprises tetrahydrofuran, the base of Step A is lithium diisopropylamide, the solvent of Step B comprises toluene and ethanol, the oxidizing agent of Step B is N-bromosuccinimide, the solvent of Step C comprises tetrahydrofuran, the base of Step C is pyridine and the solvent of Step D comprises tetrahydrofuran and water.

In one embodiment of the present invention, the compound of formula (1) is first contacted with the compound of formula (2) in a reaction mixture comprising a base and solvent, and second optionally contacted with a reaction mixture comprising an aqueous acid or base resulting in the pH of the aqueous phase to be within the range 2<pH<4, preferably pH 3. Preferably, the base is lithium diisopropylamide and the first solvent is THF, wherein the reaction mixture is maintained such that the internal temperature remains less than −5° C., preferably at −15° C. Preferably, the pH of the aqueous phase is adjusted to pH 3 with a reaction mixture comprising sulfuric acid, water and toluene.

In one embodiment of the present invention, the compound of formula (5) is contacted with the compound of formula (7) in a reaction mixture comprising the solvent THF and the base pyridine, and then the base pyridine is removed by addition of saturated saline or aqueous salt (preferably sodium chloride) solution. In one embodiment of the present invention, the compound of formula (8) is contacted with the compound of formula (IX) in a reaction mixture comprising a first solvent, such that the compound of formula (10) is formed. An aromatic solvent is then added to the mixture, followed by removal of the first solvent by distillation, resulting in the precipitation of the compound of formula (10). Preferably, the aromatic solvent is toluene.

In another aspect of the invention, provided herein is a compound according to formula (I):

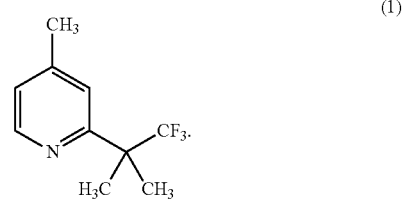

(1)

The compound of formula (1) is particularly useful as a starting material, or an intermediate, in the preparation of the compound of formula (10), as well as chemical analogues of the compound of formula (10). The compound of formula (1) can be synthesized in accordance with the preparation methods set forth in Scheme 4 or Scheme 5 herein.

The skilled practitioner will recognize several parameters of the foregoing processes that may be varied advantageously in order to obtain a desirable outcome.

These parameters include, for example, the methods and means of purification of reaction components and solvents; the order of addition of said reaction components and solvents to the reaction mixture; the duration of reaction of said reaction components and solvents; and the temperature and rate of stirring, mixing or agitation of the reaction components and solvents during said reaction.

Definitions

As used herein, the term "lower" or "$C_1$-$C_7$" denotes a radical having up to and including a maximum of 7, especially up to and including a maximum of 4 carbon atoms, the radicals in question being either linear or branched with single or multiple branching.

As used herein, the term "alkyl" refers to a straight-chain or branched-chain alkyl group, preferably represents a straight-chain or branched-chain $C_{1-12}$alkyl, particularly preferably represents a straight-chain or branched-chain $C_{1-7}$alkyl; for example, methyl, ethyl, n- or iso-propyl, n-, iso-, sec- or tert-butyl, n-pentyl, n-hexyl, n-heptyl, n-octyl, n-nonyl, n-decyl, n-undecyl, n-dodecyl, with particular preference given to methyl, ethyl, n-propyl, iso-propyl and n-butyl and iso-butyl. Alkyl may be unsubstituted or substituted. Exemplary substituents include, but are not limited to deuterium, hydroxy, alkoxy, halo and amino. An example of a substituted alkyl is trifluoromethyl. Cycloalkyl may also be a substituent to alkyl. An example of such a case is the moiety (alkyl)-cyclopropyl or alkandiyl-cyproyl, e.g. —$CH_2$-cyclopropyl. $C_1$-$C_7$-alkyl is preferably alkyl with from and including 1 up to and including 7, preferably from and including 1 to and including 4, and is linear or branched; preferably, lower alkyl is butyl, such as n-butyl, sec-butyl, isobutyl, tert-butyl, propyl, such as n-propyl or isopropyl, ethyl or preferably methyl.

Each alkyl part of other groups like "alkoxy", "alkoxyalkyl", "alkoxycarbonyl", "alkoxy-carbonylalkyl", "alkylsulfonyl", "alkylsulfoxyl", "alkylamino", "haloalkyl" shall have the same meaning as described in the above-mentioned definition of "alkyl"

As used herein, the term "alkandiyl" refers to a straight-chain or branched-chain alkandiyl group bound by two different Carbon atoms to the moiety, it preferably represents a straight-chain or branched-chain $C_{1-12}$ alkandiyl, particularly preferably represents a straight-chain or branched-chain $C_{1-6}$ alkandiyl; for example, methandiyl (—$CH_2$—), 1,2-ethanediyl (—$CH_2$—$CH_2$—), 1,1-ethanediyl ((—CH($CH_3$)—), 1,1-, 1,2-, 1,3-propanediyl and 1,1-, 1,2-, 1,3-, 1,4-butanediyl, with particular preference given to methandiyl, 1,1-ethanediyl, 1,2-ethanediyl, 1,3-propanediyl, 1,4-butanediyl.

As used herein, the term "cycloalkyl" refers to a saturated or partially saturated, monocyclic, fused polycyclic, or Spiro polycyclic, carbocycle having from 3 to 12 ring atoms per carbocycle. Illustrative examples of cycloalkyl groups include the following moieties: cyclopropyl, cyclobutyl, cyclpentyl and cylclohexyl. Cycloalkyl may be unsubstituted or substituted; exemplary substituents are provided in the definition for alkyl and also include alkyl itself (e.g. methyl). A moiety like —($CH_3$)cyclopropyl is considered substituted cycloalkyl.

As used herein, the term "aryl" refers to an aromatic homocyclic ring system (i.e. only Carbon as ring forming atoms) with 6 or more carbon atoms; aryl is preferably an aromatic moiety with 6 to 14 ring carbon atoms, more preferably with 6 to 10 ring carbon atoms, such as phenyl or naphthyl, preferably phenyl. Aryl may be unsubstituted or substituted by one or more, preferably up to three, more preferably up to two substituents independently selected from the group consisting of unsubstituted or substituted heterocyclyl as described below, especially pyrrolidinyl, such as pyrrolidino, oxopyrrolidinyl, such as oxopyrrolidino, $C_1$-$C_7$-alkyl-pyrrolidinyl, 2,5-di-($C_1$-$C_7$-alkyl)pyrrolidinyl, such as 2,5-di-($C_1$-$C_7$alkyl)-pyrrolidino, tetrahydrofuranyl, thiophenyl, $C_1$-$C_7$-alkylpyrazolidinyl, pyridinyl, $C_1$-$C_7$-alkylpiperidinyl, piperidino, piperidino substituted by amino or N-mono- or N,N-di-[lower alkyl, phenyl, $C_1$-$C_7$-alkanoyl and/or phenyl-lower alkyl)-amino, unsubstituted or N-lower alkyl substituted piperidinyl bound via a ring carbon atom, piperazino, lower alkylpiperazino, morpholino, thiomorpholino, S-oxo-thiomorpholino or S,S-dioxothiomorpholino; $C_1$-$C_7$-alkyl, amino-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, carbamoyl-$C_1$-$C_7$-alkyl, [N-mono- or N,N-di-($C_1$-$C_7$-alkyl)-carbamoyl]-$C_1$-$C_7$-alkyl, $C_1$-$C_7$-alkanesulfinyl-$C_1$-$C_7$-alkyl, $C_1$-$C_7$-alkanesulfonyl-$C_1$-$C_7$-alkyl, phenyl, naphthyl, mono- to tri-[$C_1$-$C_7$-alkyl, halo and/or cyano]-phenyl or mono- to tri-[$C_1$-$C_7$-alkyl, halo and/or cyano]-naphthyl; $C_3$-$C_8$-cycloalkyl, mono- to tri-[$C_1$-$C_7$-alkyl and/or hydroxy]-$C_3$-$C_8$-cycloalkyl; halo, hydroxy, lower alkoxy, lower-alkoxy-lower alkoxy, (lower-alkoxy)-lower alkoxy-lower alkoxy, halo-$C_1$-$C_7$-alkoxy, phenoxy, naphthyloxy, phenyl- or naphthyl-lower alkoxy; amino-$C_1$-$C_7$-alkoxy, lower-alkanoyloxy, benzoyloxy, naphthoyloxy, formyl (CHO), amino, N-mono- or N,N-di-($C_1$-$C_7$-alkyl)-amino, $C_1$-$C_7$-alkanoylamino, $C_1$-$C_7$-alkanesulfonylamino, carboxy, lower alkoxy carbonyl, e.g.; phenyl- or naphthyl-lower alkoxycarbonyl, such as benzyloxycarbonyl; $C_1$-$C_7$-alkanoyl, such as acetyl, benzoyl, naphthoyl, carbamoyl, N-mono- or N,N-disubstituted carbamoyl, such as N-mono- or N,N-di-substituted carbamoyl wherein the substitutents are selected from lower alkyl, (lower-alkoxy)-lower alkyl and hydroxy-lower alkyl; amidino, guanidino, ureido, mercapto, lower alkylthio, phenyl- or naphthylthio, phenyl- or naphthyl-lower alkylthio, lower alkyl-phenylthio, lower alkyl-naphthylthio, halo-lower alkylmercapto, sulfo (—$SO_3H$), lower alkanesulfonyl, phenyl- or naphthyl-sulfonyl, phenyl- or naphthyl-lower alkylsulfonyl, alkylphenylsulfonyl, halo-lower alkylsulfonyl, such as trifluorome-thanesulfonyl; sulfonamido, benzosulfonamido, azido, azido-$C_1$-$C_7$-alkyl, especially azidomethyl, $C_1$-$C_7$-alkanesulfonyl, sulfamoyl, N-mono- or N,N-di-($C_1$-$C_7$-alkyl)-sulfamoyl, morpholinosulfonyl, thiomorpholinosulfonyl, cyano and nitro; where each phenyl or naphthyl (also in phenoxy or naphthoxy) mentioned above as substituent or part of a substituent of substituted alkyl (or also of substituted aryl, heterocyclyl etc. mentioned herein) is itself unsubstituted or substituted by one or more, e.g. up to three, preferably 1 or 2, substituents independently selected from halo, halo-lower alkyl, such as trifluoromethyl, hydroxy, lower alkoxy, azido, amino, N-mono- or N,N-di-(lower alkyl and/or $C_1$-$C_7$-alkanoyl)-amino, nitro, carboxy, lower-alkoxycarbonyl, carbamoyl, cyano and/or sulfamoyl.

The term "aryloxy" refers to a moiety comprising an oxygen atom that is substituted with an aryl group, as defined above.

The term "heteroaryl," as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is nonaromatic or contains no heteroatoms, it is understood that attachment is via the aromatic ring or via the heteroatom containing ring, respectively.

As used herein, the term "heterocycle" or "heterocyclyl" refers to a heterocyclic radical that is unsaturated (=carrying the highest possible number of conjugated double bonds in the ring(s)), saturated or partially saturated and is preferably a monocyclic or in a broader aspect of the invention bicyclic, tricyclic or spirocyclic ring; and has 3 to 24, more preferably 4 to 16, most preferably 5 to 10 and most preferably 5 or 6 ring atoms; wherein one or more, preferably one to four, especially one or two ring atoms are a heteroatom (the remaining ring atoms therefore being carbon). The bonding ring (i.e. the ring connecting to the molecule) preferably has 4 to 12, especially 5 to 7 ring atoms. The term heterocyclyl also includes heteroaryl. The heterocyclic radical (heterocyclyl) may be unsubstituted or substituted by one or more, especially 1 to 3, substituents independently selected from the group consisting of the substituents defined above for substituted alkyl and/or from one or more of the following substituents: oxo (═O), thiocarbonyl (═S), imino (═NH), imino-lower alkyl. Further, heterocyclyl is especially a heterocyclyl radical selected from the group consisting of oxiranyl, azirinyl, aziridinyl, 1,2-oxathiolanyl, thienyl (=thiophenyl), furanyl, tetrahydrofuryl, pyranyl, thiopyranyl, thianthrenyl, isobenzofuranyl, benzofuranyl, chromnenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidinyl, piperazinyl, pyridazinyl, morpholinyl, thiomorpholinyl, (S-oxo or S,S-dioxo)-thiomorpholinyl, indolizinyl, azepanyl, diazepanyl, especially 1,4-diazepanyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, beta-carbolinyl, phenanthridinyl, acridinyl, perimidinyl, phenanthrolinyl, furazanyl, phenazinyl, phenothiazinyl, phenoxazinyl, chromenyl, isochromanyl, chromanyl, benzo[1,3]dioxol-5-yl and 2,3-dihydrobenzo[1,4]dioxin-6-yl, each of these radicals being unsubstituted or substituted by one or more, preferably up to three, substituents selected from those mentioned above for substituted aryl and/or from one or more of the following substituents: oxo (═O), thiocarbonyl (═S), imino (═NH), imino-lower alkyl.

The term "heteroatoms" are atoms other than Carbon and Hydrogen, preferably nitrogen (N), oxygen (O) or sulfur (S), in particular nitrogen.

Moreover, the alkyl, alkoxy, aryl, aryloxy and heteroaryl groups described above can be "unsubstituted" or "substituted." The term "substituted" is intended to describe moieties having substituents replacing a hydrogen on one or more atoms, e.g. C, O or N, of a molecule. Such substituents can independently include, for example, one or more of the following: straight or branched alkyl (preferably $C_1$-$C_5$), cycloalkyl (preferably $C_3$-$C_8$), alkoxy (preferably $C_1$-$C_6$), thioalkyl (preferably $C_1$-$C_6$), alkenyl (preferably $C_2$-$C_6$), alkynyl (preferably $C_2$-$C_6$), heterocyclic, carbocyclic, aryl (e.g., phenyl), aryloxy (e.g., phenoxy), aralkyl (e.g., benzyl), aryloxyalkyl (e.g., phenyloxyalkyl), arylacetamidoyl, alkylaryl, heteroaralkyl, alkylcarbonyl and arylcarbonyl or other such acyl group, heteroarylcarbonyl, or heteroaryl group, $(CR'R'')_{0-3}NR'R''$ (e.g., —$NH_2$), $(CR'R'')_{0-3}CN$ (e.g., —CN), —$NO_2$, halogen (e.g., —F, —Cl, —Br, or —I), $(CR'R'')_{0-3}C(halogen)_3$ (e.g., —$CF_3$), $(CR'R'')_{0-3}CH(halogen)_2$, $(CR'R'')_{0-3}CH_2(halogen)$, $(CR'R'')_{0-3}CONR'R''$, $(CR'R'')_{0-3}(CNH)NR'R''$, $(CR'R'')_{0-3}S(O)_{1-2}NR'R''$, $(CR'R'')_{0-3}$ CHO, $(CR'R'')_{0-3}O(CR'R'')_{0-3}H$, $(CR'R'')_{0-3}$ $S(O)_{0-3}$ R' (e.g., —$SO_3H$, —$OSO_3H$), $(CR'R'')_{0-3}O$ $(CR'R'')_{0-3}$ H (e.g., —$CH_2OCH_3$ and —$OCH_3$), $(CR'R'')_{0-3}$ $S(CR'R'')_{0-3}$ H (e.g., —SH and —$SCH_3$), $(CR'R'')_{0-3}OH$ (e.g., —OH), $(CR'R'')_{0-3}$ COR', $(CR'R'')_{0-3}$ (substituted or unsubstituted phenyl), $(CR'R'')_{0-3}(C_3$-$C_8$ cycloalkyl), $(CR'R'')_{0-3}CO_2R'$ (e.g., —$CO_2H$), or $(CR'R'')_{0-3}OR'$ group, or the side chain of any naturally occurring amino acid; wherein R' and R" are each independently hydrogen, a $C_1$-$C_5$ alkyl, $C_2$-$C_5$ alkenyl, $C_2$-$C_5$ alkynyl, or aryl group.

As used herein, the term "halogen" or "halo" refers to fluorine, bromine, chlorine or iodine, in particular fluorine, chlorine. Halogen-substituted groups and moieties, such as alkyl substituted by halogen (haloalkyl) can be mono-, poly- or per-halogenated.

The term "amine" or "amino" should be understood as being broadly applied to both a molecule, or a moiety or functional group, as generally understood in the art, and may be primary, secondary, or tertiary. The term "amine" or "amino" includes compounds where a nitrogen atom is covalently bonded to at least one carbon, hydrogen or heteroatom. The terms include, for example, but are not limited to, "alkyl amino," "arylamino," "diarylamino," "alkylarylamino," "alkylaminoaryl," "arylaminoalkyl," "alkaminoalkyl," "amide," "amido," and "aminocarbonyl." The term "alkyl amino" comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

Examples

Abbreviations

The following abbreviations are used in the figures and text: THF (tetrahydrofuran); RT (room temperature); $iPr_2NH$ (diisopropylamine); $iPr_2NLi$ (lithium diisopropylamide); LDA (lithium diisopropylamide); $H_2SO_4$ (sulfuric acid); $H_2O$ (water); IPA (isopropyl acetate); NaCl (sodium chloride); MsCl (methanesulfonyl chloride); NaH (sodium hydride); n-BuLi (n-butyllithium); $SF_4$ (sulfur tetrafluoride); HCl (hydrochloric acid); HF (hydrofluoric acid).

Synthesis Procedures

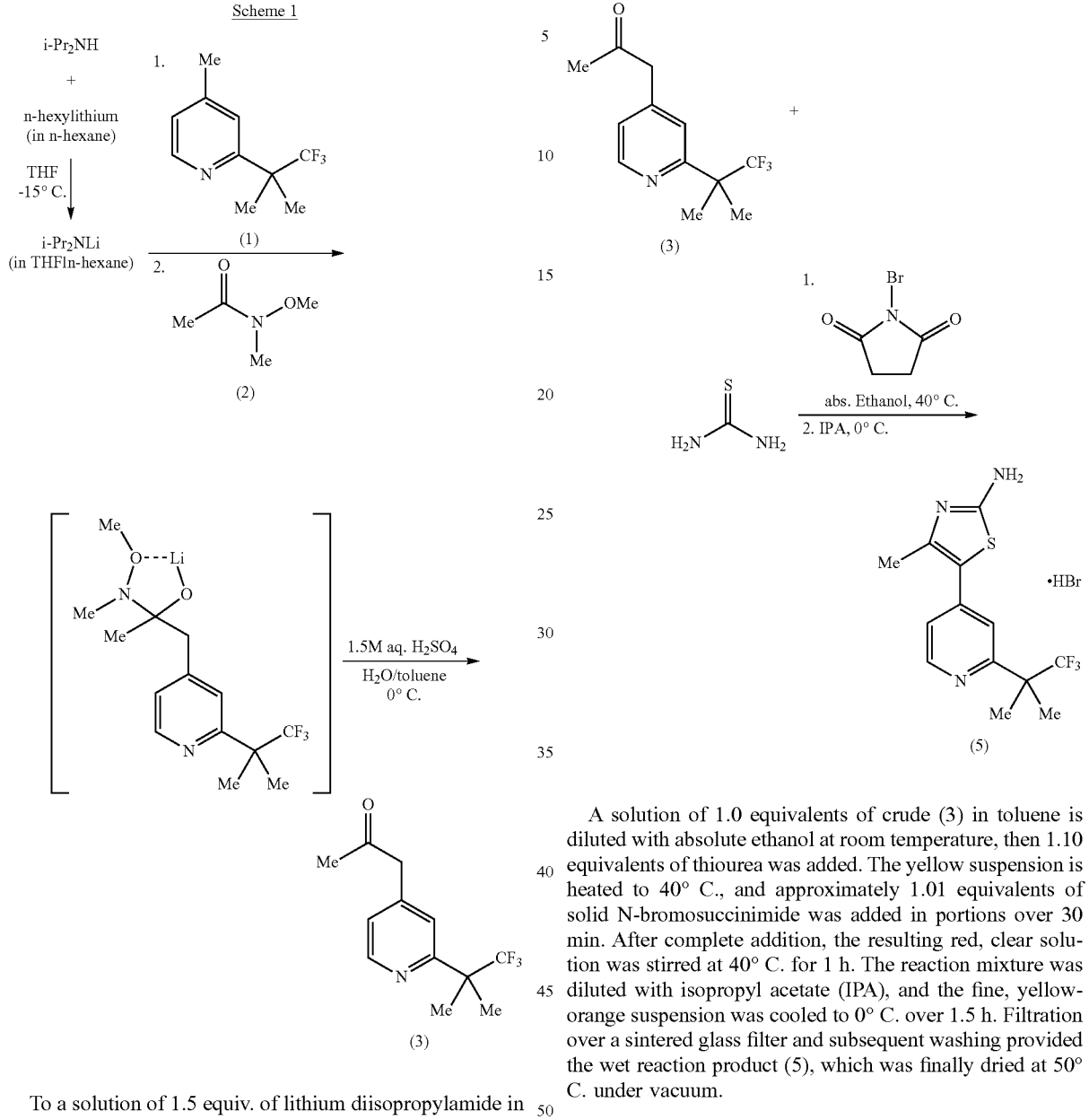

To a solution of 1.5 equiv. of lithium diisopropylamide in THF at −15° C., freshly prepared from n-hexyllithium and diisopropylamine, was added a solution of 1.0 equiv. of building block (1) in THF over 30 min. The resulting deep brown-red solution was then stirred at −15° C. for 30 min. Subsequently, a solution of 1.15 equiv. of Weinreb amide (2) in THF was added over 30 min, and the reaction stirred at −15° C. for 1 h before being transferred onto a mixture of 1.5 molar aqueous sulfuric acid and toluene at 10° C. The biphasic mixture was vigorously stirred at room temperature for 25 min. Care was taken that the aqueous layer stayed at 2<pH<4, preferably pH 3. After phase separation, the organic layer was washed with water, then concentrated at 50° C. under vacuum to ca. 15-20% of its original volume to provide a solution of crude ketone (3) in toluene.

A solution of 1.0 equivalents of crude (3) in toluene is diluted with absolute ethanol at room temperature, then 1.10 equivalents of thiourea was added. The yellow suspension is heated to 40° C., and approximately 1.01 equivalents of solid N-bromosuccinimide was added in portions over 30 min. After complete addition, the resulting red, clear solution was stirred at 40° C. for 1 h. The reaction mixture was diluted with isopropyl acetate (IPA), and the fine, yellow-orange suspension was cooled to 0° C. over 1.5 h. Filtration over a sintered glass filter and subsequent washing provided the wet reaction product (5), which was finally dried at 50° C. under vacuum.

-continued

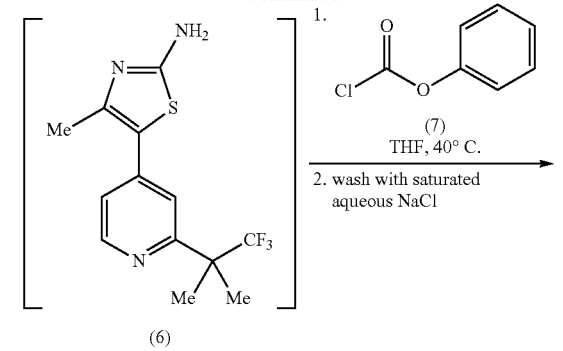

(6)

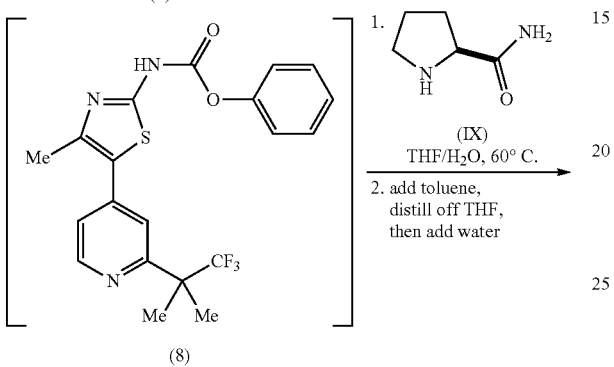

(8)

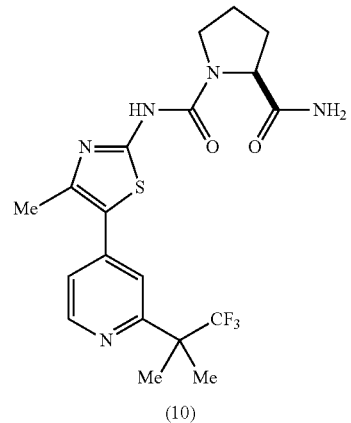

(10)

To a yellow suspension of 1.0 equivalents of compound (5) in THF at room temperature was added 2.0 equivalents of pyridine. The reaction mixture was heated to 40° C., then a solution of 1.0 equivalents of phenyl chloroformate (7) in THF was added over 30 min. After stirring at 40° C. for 1 h, the reaction was cooled to RT, then saturated aqueous NaCl solution was added, and the biphasic mixture was stirred at RT for 10 min before phase separation. The organic layer was heated to 60° C., then a solution of 1.0 equivalents of L-prolinamide (IX) in water was added over 30 min. The reaction was stirred at 60° C. for 2 h, then the reaction mixture was cooled to 50° C., then toluene was added, followed by removal of THF via distillation under vacuum. The resulting suspension was treated with water, and the reaction mixture was stirred at 50° C. for 30 min, before being cooled to 10° C. over 2 h. After stirring at 10° C. for another 30 min, the off-white suspension was filtered, and the filter cake washed with toluene, then dried at 50° C. under vacuum to give (10).

Scheme 4

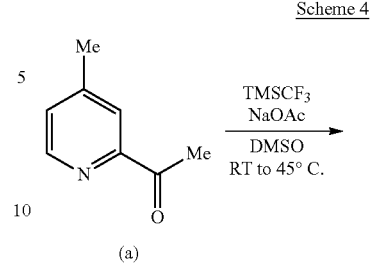

(a)

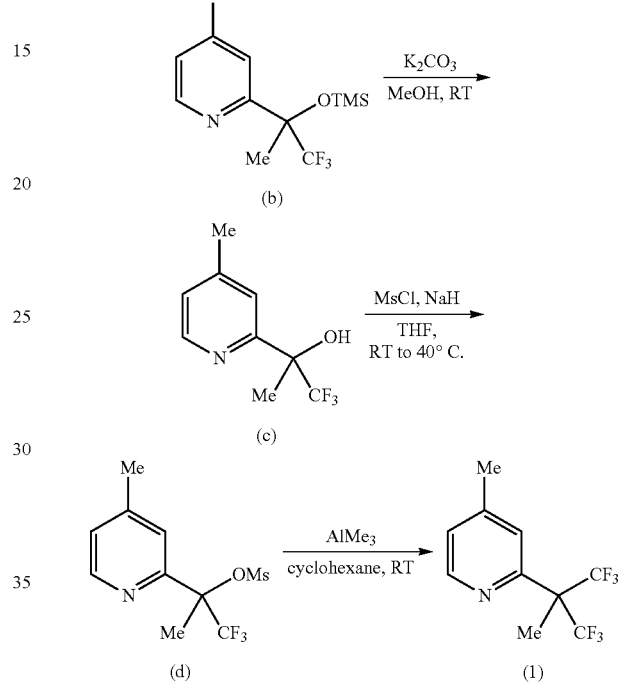

4-Methyl-2-(2,2,2-trifluoro-1-methyl 1-trimethylsilanyloxy-ethyl)pyridine (b)

To a fine, white suspension of sodium acetate (96.0 g, 117 mmol, 1.0 equiv.) in 1 L DMSO was added 2-acetyl-4-methylpyridine (158 g, 117 mmol, 1.0 equiv.). After dilution with another 0.5 L DMSO, trimethyl-trifluoromethylsilane (375 g, 264 mmol, 2.2 equiv.) was added over 75 minutes. During the addition, the reaction vessel was placed in a cooling bath at 10° C. to keep the internal temperature between 20-25°. The resulting dark suspension was stirred at room temperature over night, then quenched carefully by addition of 1.5 L water over 20 minutes. During the addition of water, the reaction vessel was placed in a cooling bath at −5° C. to keep the internal temperature between 10-25° C. After stirring at room temperature for 45 minutes, the mixture was diluted with 3 L ethyl acetate and stirred for another 15 minutes. The phases were separated, and the water layer was extracted with 2 L ethyl acetate. The combined organic phases were washed with 3 L saturated aqueous NaHCO₃, dried over MgSO₄, filtered and concentrated in vacuo to give 346 g (106%, 88.6 area % by HPLC) of trifluoromethyl compound (b) as a brown, intensively smelling oil.

1,1,1-Trifluoro-2-(4-methylpyridin-2-yl)propan-2-ol (c)

To a solution of 4-methyl-2-(2,2,2-trifluoro-1-methyl-1-trimethylsilanyloxy-ethyl)pyridine (b) (346 g, 125 mmol, 1.0 equiv.) in 1.5 L MeOH at room temperature was added solid $K_2CO_3$ (344 g, 249 mmol, 2.0 equiv.). The resulting beige suspension was stirred at room temperature for 1 hour, then filtered over filter paper. The filtrate was concentrated in vacuo to give a solid, intensively smelling residue. The residue was dissolved in 1 L ethyl acetate and washed with water (2×1 L). After drying over $MgSO_4$ and filtration, concentration in vacuo provided 252 g (98%) of alcohol (c) as an oil.

1,1,1-Trifluoro-2-(4-methylpyridin-2-yl)propan-2-yl methanesulfonate (d)

To a suspension of NaH (60% in mineral oil, 23.4 g, 585 mmol, 1.5 equiv.) in 1 L THF at 0° C. was added a solution of 1,1,1-trifluoro2-(4-methylpyridin-2-yl)propan-2-ol (c) (80 g, 390 mmol, 1.0 equiv.) in 200 ml THF dropwise over 34 minutes. Gas evolution occurred, and the reaction mixture turned brownish. The reaction was warmed to 40° C. and stirred at 40° C. for 45 minutes, when gas evolution had ceased. After cooling to room temperature, a solution of methanesulfonyl chloride (45.6 ml, 585 mmol, 1.5 equiv.) in 50 ml THF was added dropwise over 30 minutes. The internal temperature rose to 36° C., and the reaction mixture turned into a light brown suspension. The reaction mixture was warmed to 40° C. and stirred at this temperature for 15 minutes, then cooled to room temperature and further stirred over night. The reaction was carefully quenched by addition of 750 ml water with cooling in an ice bath. The resulting brown biphasic mixture was stirred at room temperature for 30 minutes, then the phases were separated. The aqueous layer was extracted with 750 ml ethyl acetate, and the combined organic phases were washed with saturated aqueous $NaHCO_3$. Drying over $MgSO_4$, filtration and concentration in vacuo provided a beige solid. The residue was redissolved in 300 ml ethyl acetate to give a turbid solution, then filtered over a plug of silica gel (120 g) and eluted with 600 ml ethyl acetate. Concentration in vacuo provided a beige solid which was redissolved in 400 ml heptane and 150 ml ethyl acetate at reflux. After hot filtration over a fritted funnel, the product crystallized at 0° C. The crystals were collected by filtration, washed with cold heptane/ethyl acetate 8:3 (2×80 ml) and dried (50° C., 10 mbar) over night to give 94.0 g (85%) of mesylate (d) as white crystals.

4-methyl-2-(1,1,1-trifluoro-2-methylpropan-2-yl)pyridine (1)

To a suspension of 1,1,1-trifluoro-2-(4-methylpyridin-2-yl)propan-2-yl methanesulfonate (d) (5.68 g, 20.1 mmol, 1.0 equiv.) in 60 ml cyclohexane at 10° C. was added $AlMe_3$ in hexane (2.0 M, 15.0 ml, 30 mmol, 23.0 equiv.) dropwise over 15 minutes. The reaction was warmed at room temperature and stirred at room temperature for 3 hours. The mixture was quenched by careful addition to 100 ml water at 0° C. and stirred at room temperature for 15 minutes. After filtration over a plug of cellflock and elution with ethyl acetate, the phases were separated. The aqueous layer was extracted with ethyl acetate, and the combined organic phases were washed with water and saturated aqueous NaCl. After drying over $Na_2SO_4$, filtration and concentration in vacuo provided a slightly brownish oil, which was purified by chromatography on siliga gel (hexane/TBME 9:1) to provide 1.15 g (28%) of the desired compound (1) as a colorless oil.

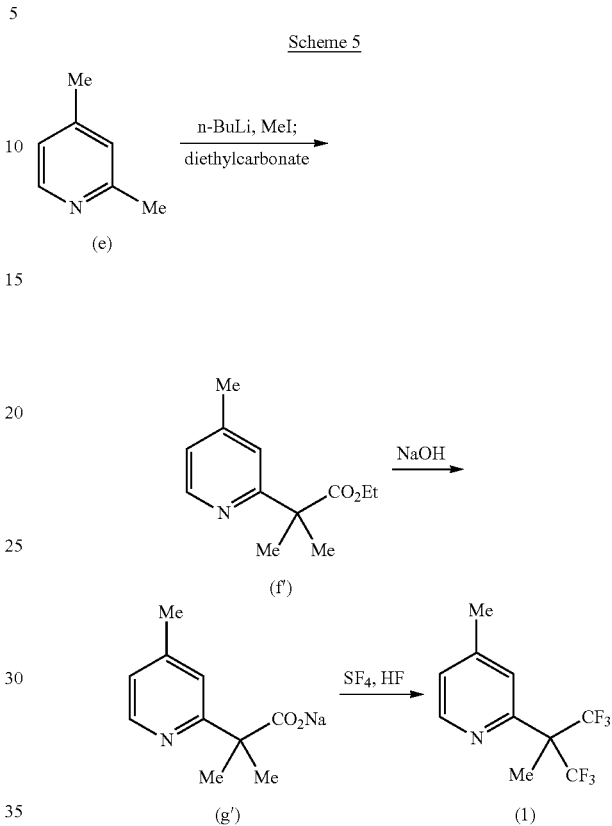

Scheme 5

To a solution of n-butyllithium (2.04 equiv.) in 2-methyltetrahydrofuran at maximum −40° C. was added a solution of 2,4-dimethylpyridine (e) (2.02 equiv.) in 2-methyltetrahydrofuran over 60 min, keeping the temperature below −30° C. The reaction mixture was stirred for 30 min at maximum −30° C. A solution of diethyl carbonate (1.00 equiv.) in 2-methyltetrahydrofuran was added over 60 min, keeping the temperature below −30° C. The reaction was warmed to room temperature, and then stirred at this temperature for 5 h. After cooling to 0° C., methyl iodide (2.15 equiv.) was charged over 40 min, keeping the temperature below 25° C. The reaction was further stirred at room temperature for 1 h, then 1 M HCl was added, and the pH was adjusted to a value of pH 8-9. After stirring for 15 min, the phases were separated, and the organic phase was washed with water. Distillation at 35° C. under vacuum then provided crude dimethylated ester (f'). Ester (f') was subsequently added to a solution of sodium hydroxide (1.05 equiv.) in ethanol at 78° C. over 2 h. More ethanol was added, and the reaction was stirred at 78° C. for 10 h. The volume was reduced to approximately 50% by distillation under normal pressure. After cooling to room temperature, tert-butyl methyl ether was added, and the reaction mixture was stirred at this temperature for 30 min. Filtration was performed after cooling to 5-10° C., and the filter cake was washed with dichloromethane. The wet product was dried at 60-70° C. under vacuum to give sodium carboxylate (g'). Compound (g') was reacted with sulfur tetrafluoride and hydrofluoric acid to afford compound (1).

The invention claimed is:
1. The compound according to formula (1):
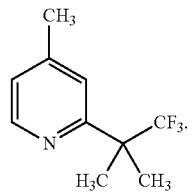
(1)
\* \* \* \* \*